United States Patent
Hemstreet, III et al.

(10) Patent No.: US 6,372,450 B1
(45) Date of Patent: *Apr. 16, 2002

(54) METHOD OF TREATING CELLS

(75) Inventors: George P. Hemstreet, III; Robert E. Hurst; Rebecca B. Bonner, all of Oklahoma City, OK (US)

(73) Assignee: Southpac Trust Int'l. Inc.

( * ) Notice: Subject to any disclaimer, the term of this patent is extended or adjusted under 35 U.S.C. 154(b) by 0 days.

This patent is subject to a terminal disclaimer.

(21) Appl. No.: 09/711,495

(22) Filed: Nov. 13, 2000

Related U.S. Application Data

(62) Division of application No. 09/165,455, filed on Oct. 2, 1998, now Pat. No. 6,194,165, which is a division of application No. 08/821,378, filed on Mar. 20, 1997, now Pat. No. 5,824,495, which is a continuation-in-part of application No. 08/605,342, filed on Feb. 9, 1996, now Pat. No. 5,741,648, which is a continuation of application No. 07/984,191, filed on Nov. 20, 1992, now Pat. No. 5,733,721.

(51) Int. Cl.[7] .................................. C12Q 1/06
(52) U.S. Cl. .................. 435/40.5; 435/40.51; 435/7.21; 435/975; 435/7.2; 435/40.52; 435/412
(58) Field of Search ............................. 435/40.5, 40.51, 435/7.21, 975, 7.2, 40.52, 412

(56) References Cited

U.S. PATENT DOCUMENTS

| | | | |
|---|---|---|---|
| 3,975,156 A | 8/1976 | Kraft et al. | 23/230 |
| 4,534,881 A | 8/1985 | Sikes et al. | 252/180 |
| 4,992,365 A | 2/1991 | Hyman | 435/34 |

OTHER PUBLICATIONS

"Fix & Perm—Applications Guide to Intracellular Flow Cytometry" CALTAG Catalog, CALTAG Laboratories, Inc. Burlingame, CA, Aug. 1996.

W.L. Parry et al., "Cancer Detection By Quantitative Fluorescence Image Analysis", *The Journal of Urology*, vol. 139, Feb. 1988, pp. 270–274.

P. L. Jones et al., Quantitative Immunofluorescence, Anti–ras p21 Antibody Specificity, and Cellular Oncoprotein Levels, *Biochemical and Biophysical Research Communications*, vol. 167, No. 2, 1990, pp. 464–470.

J.Y. Rao et al., "Cellular F–Actin Levels as a Marker for Cellular Transformation: Relationship to Cell Division and Differentiation", *Cancer Research*, 50, Apr. 1990, pp. 2215–2220.

Rodriguez et al., *Recombinant DNA Techniques: An Introduction*, The Benjamin/Cummings Publishing Company, Inc., Menlo Park California, pp. 200–201, 1983.

Kagedal et al., "Automated High–Performance Liquid Chromatographic Determination of 5–s Cysteinyl–3 4–Dihydroxyphenylalanine in Urine," *J Chromatogr*, 473(2), Abstract 7175415.

*Primary Examiner*—Bao-Thuy L. Nguyen
(74) *Attorney, Agent, or Firm*—Dunlap Codding & Rogers PC

(57) ABSTRACT

A composition and treatment method for fixating cells and for preparing them for examination. In particular, the invention contemplates compositions effective in inhibiting crystal formation in the cell sample and effective in enhancing cell adherence to examination slides.

15 Claims, 6 Drawing Sheets

Figure 1. Crystals observed in the absence of chelating agent (control).
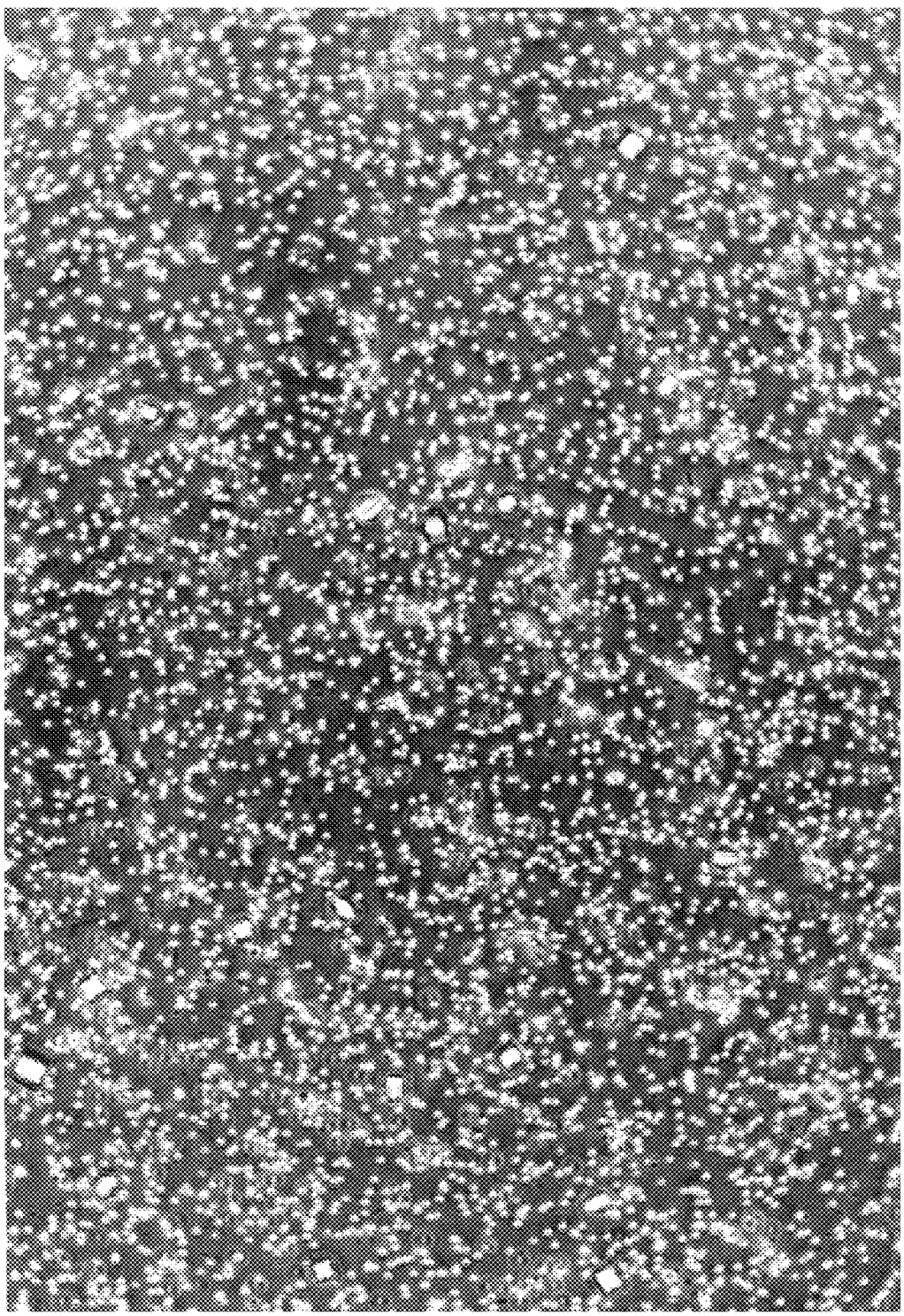

Figure 2. Crystals observed in the presence of a calcium chelating resin, Chelex 100, 50 mg.
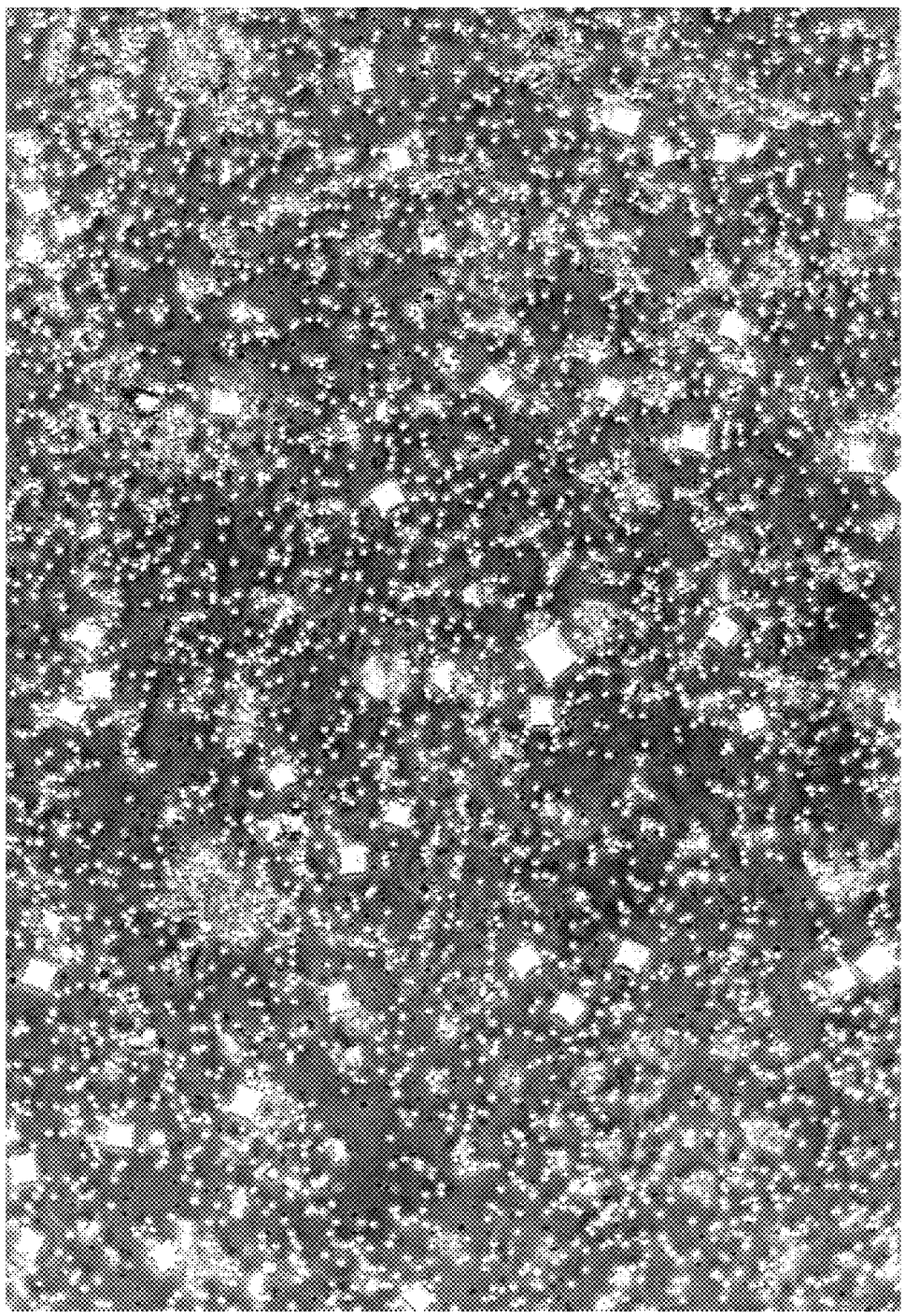

Figure 3. Crystals observed in the presence of 0.01 M of the dipotassuim salt of ethylenediaminetetra acid (KEDTA).
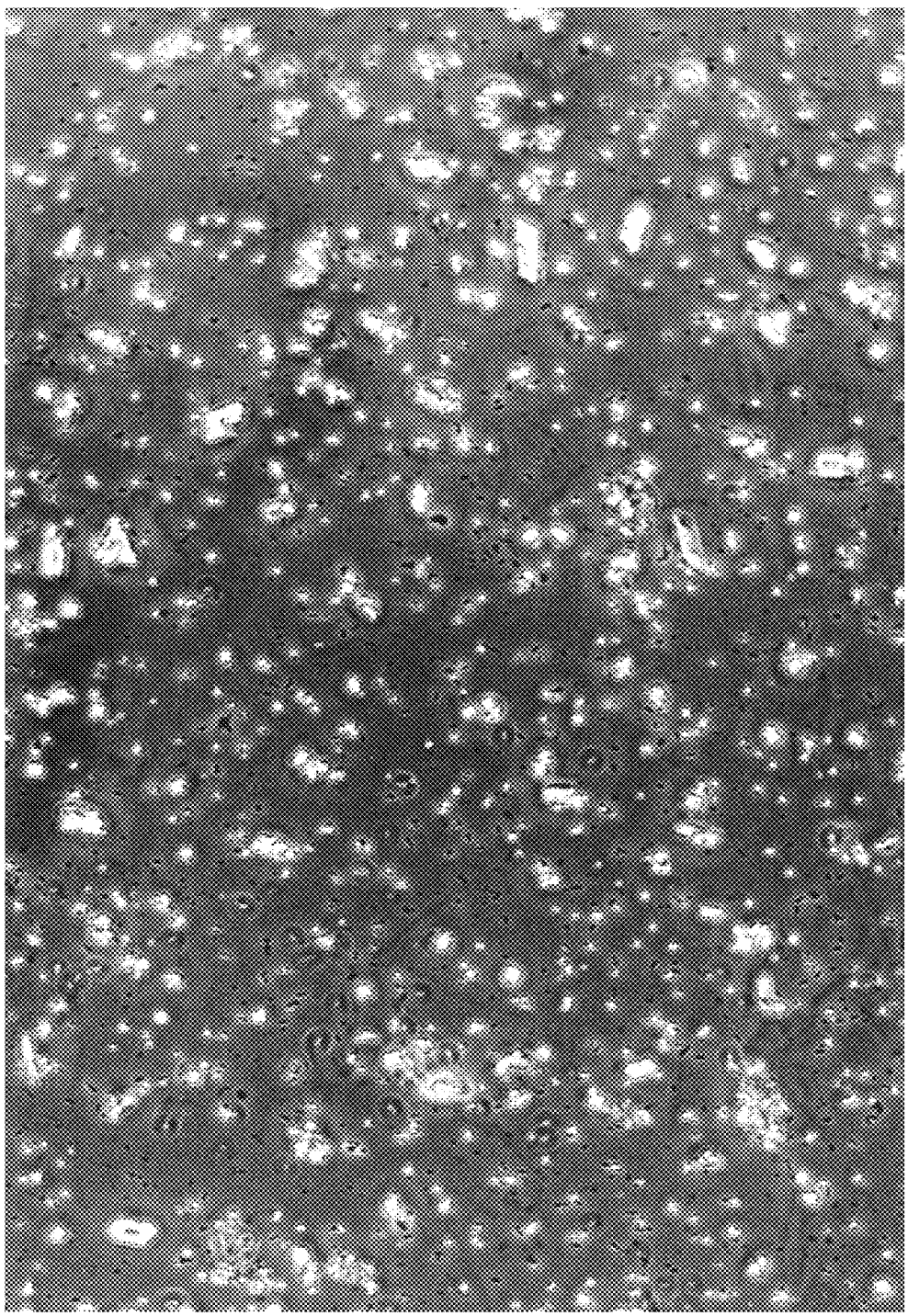

Figure 4. Crystals observed in the presence of 0.01 M of the potassium salt of Ethylene glycol-bis[beta-aminoethyl ether]-N,N,N$^1$,N$^1$-tetraacetic acid (KEGTA).
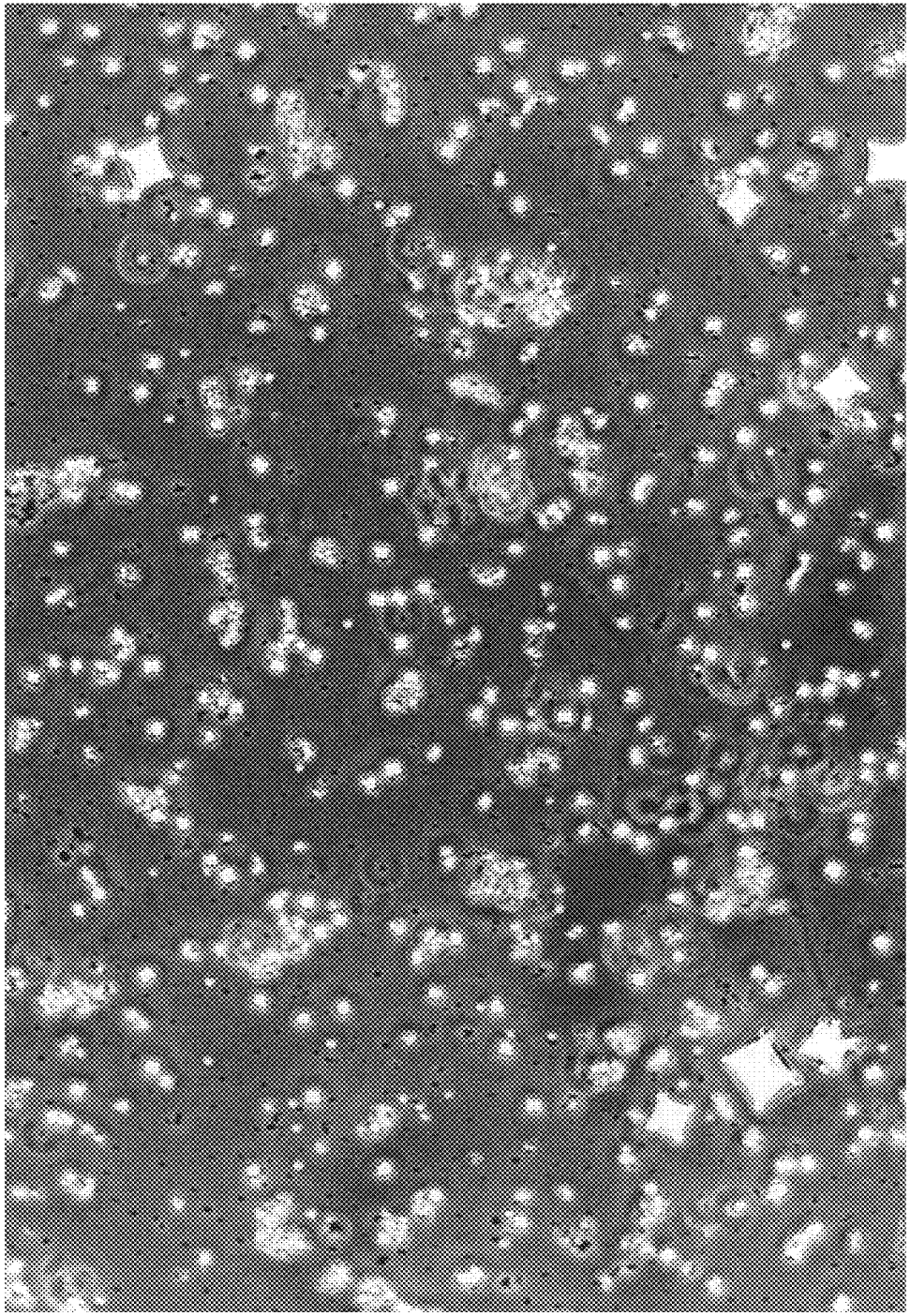

Figure 5. Crystals observed in the presence of 0.01 M of the potassium salt of trans-1,2-Diaminocyclohexane-N,N,N¹,N¹-tetraacetic (KCDTA).
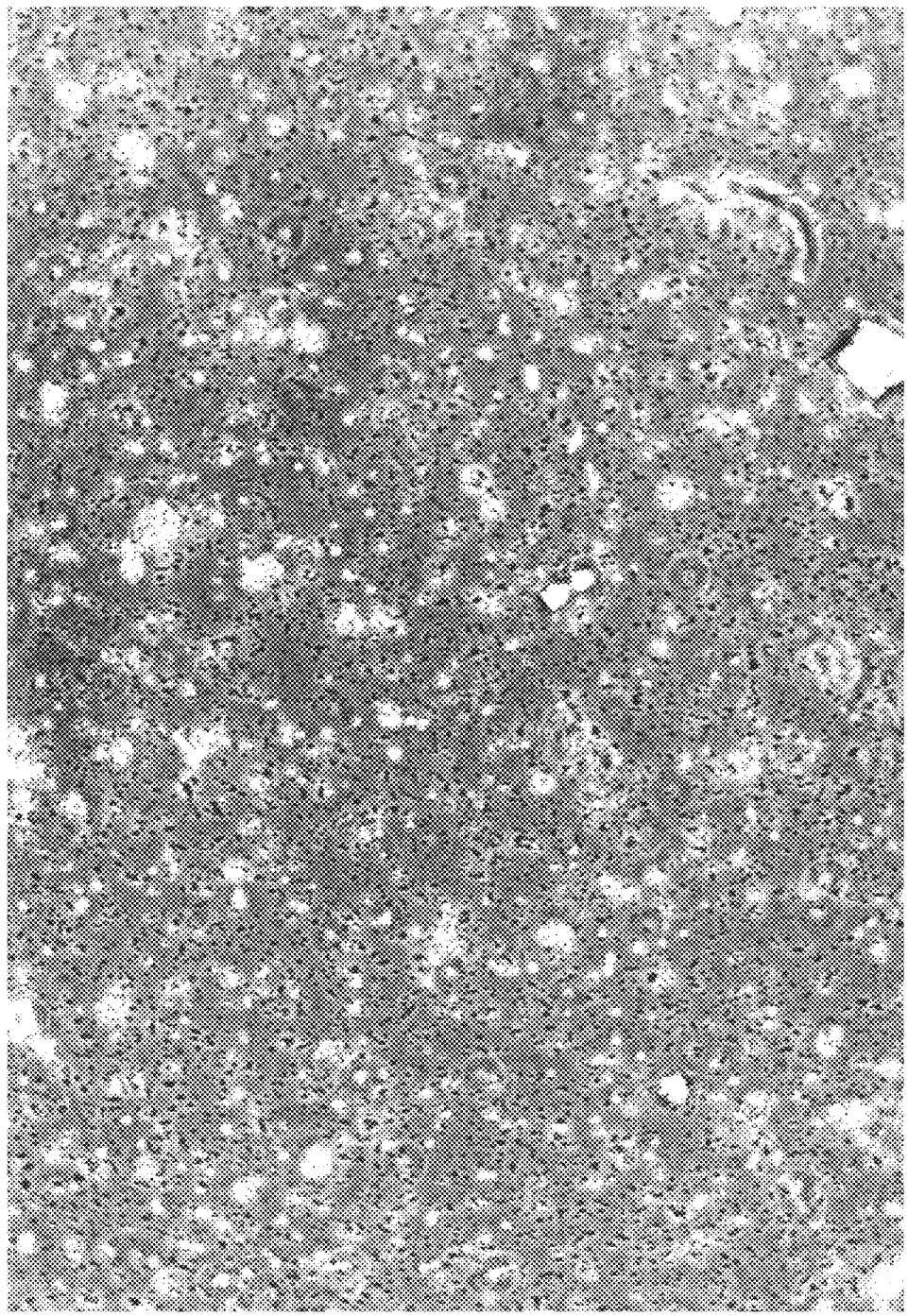

Figure 6. Crystals observed in the presence of 0.01 M of the potassium salt of 1,2-bis(2-aminophenoxy)ethane-N,N,N$^1$,N$^1$-tetraacetic acid (KBAPTA).
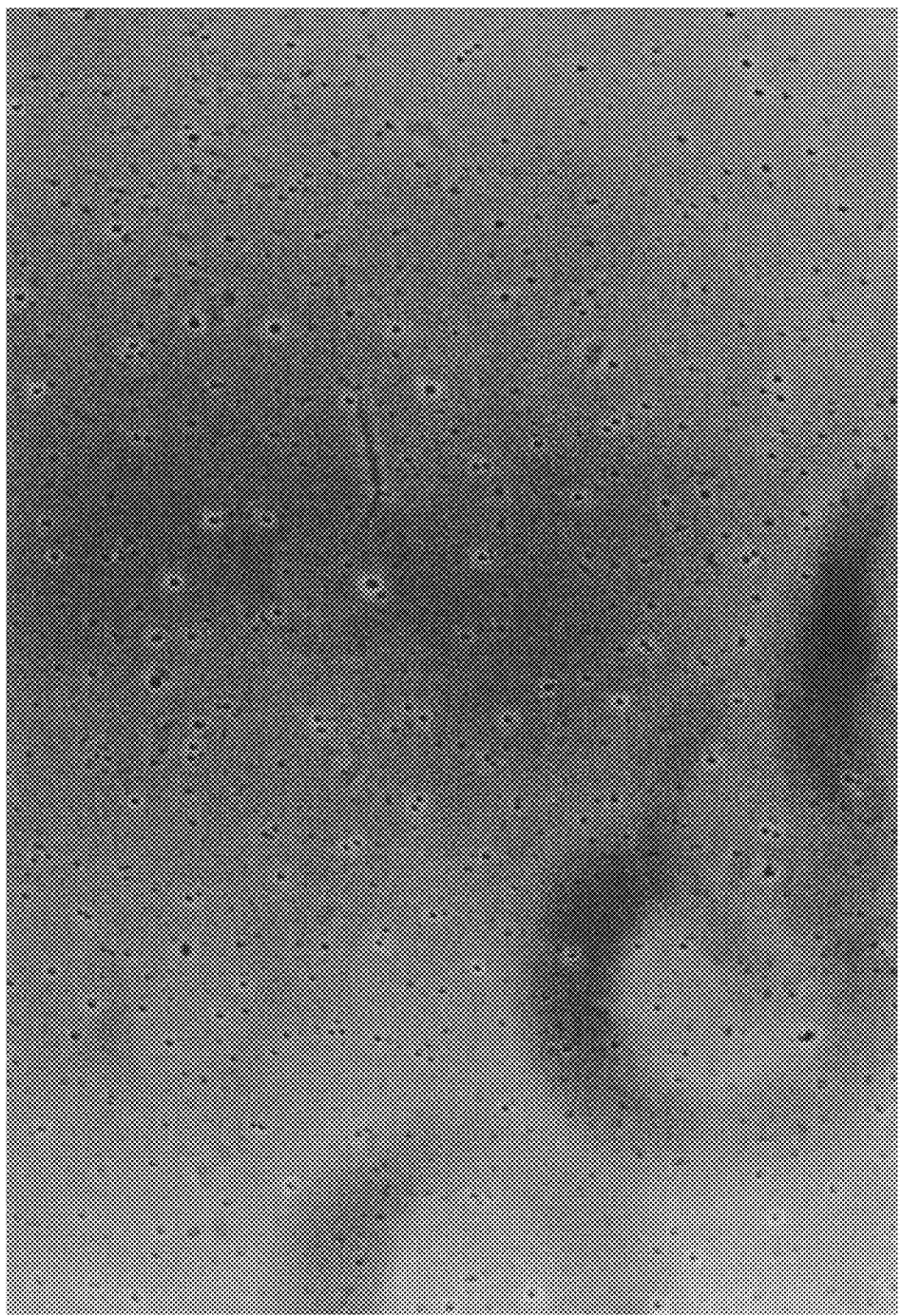

METHOD OF TREATING CELLS

CROSS-REFERENCE TO RELATED APPLICATIONS

This is a divisional of U.S. Ser. No. 09/165,455 filed Oct. 2, 1998 now U.S. Pat. No. 6,194,165, which is a continuation of U.S. Ser. No. 08/821,378 filed Mar. 20, 1997, and issuing on Oct. 20, 1998 as U.S. Pat. No. 5,824,495, which is a continuation-in-part of U.S. Ser. No. 08/605,342, filed Feb. 9, 1996, now U.S. Pat. No. 5,741,648 issued Apr. 21, 1998, which is a continuation of U.S. Ser. No. 07/984,191, filed Nov. 20, 1992, now U.S. Pat. No. 5,733,721 issued Mar. 31, 1998, the specification of which is hereby incorporated herein by reference in its entirety.

BACKGROUND

This invention relates to compositions which are used to prepare cell samples for cytological examination, especially where the samples are urine or bladder wash samples or fine needle aspirations of prostate or kidney tissues or organs.

Cytologic analyses are often carried out in central laboratories. Preparation and preservation of the cells and minimization of artifacts is a crucial consideration in shipping samples to central laboratories. With urine samples, among the more common interfering artifacts are crystals that form from the oxalates and phosphates within the urine. Although other substances in the urine can also form crystals, by far the most common are phosphates and oxalates. The crystals can sometimes be so dense as to obscure the cells, interfere with proper staining of the cells, interfere with adherence of the cells to microscope slides, or complicate the analysis of the cells.

In spite of the problems caused by crystal formation within urine and bladder wash samples, there are no cell fixative or preservative compositions for fixing urine which are effective in inhibiting the formation of crystals.

A cell preparative composition which preserved the cells with the retention of the characteristic cell morphology and which simultaneously inhibited crystal formation in the sample or dissolved crystals already within the sample and which also promoted adherence of cells to examination slides would be of great value in the field of cytological analyses.

BRIEF DESCRIPTION OF THE DRAWINGS

FIG. 1 is a photomicrograph of a urine sample preserved only with ethanol and showing numerous crystals.

FIG. 2 is a photomicrograph of a urine sample treated with a commercially-available chelating resin and showing numerous crystals.

FIG. 3 is a photomicrograph of a urine sample treated with one version of the present invention (including KEDTA).

FIG. 4 is a photomicrograph of a urine sample treated with another version of the present invention (including KCDTA).

FIG. 5 is a photomicrograph of a urine sample treated with yet another version of the present invention (including KEGTA).

FIG. 6 is a photomicrograph of a urine sample treated with still another version of the present invention (including KBAPTA).

DESCRIPTION

The present invention contemplates a fixative/preservative solution which preserves the cells in a urological sample with retention of characteristic morphology and quantity and concentration and distribution of biomarkers in the cells while simultaneously inhibiting the formation of crystals or dissolving crystals therein and which promotes adherence of the cells to slides. The present invention further contemplates a kit comprising this composition or materials for its production and a method of use of this fixative composition or kit for shipment and storage of the preserved cell sample. Inhibition of crystal formation in such samples is important because crystals can (1) prevent or interfere with adherence of cells to a slide, (2) lengthen the time necessary to prepare the slide for analysis, and (3) physically obscure the viewing of cells on the slide. The benefits to the reduction of crystal formation in the sample are to (1) decrease preparation time, (2) decrease the number of unsatisfactory slides which are produced, and (3) increase the number of cells per microscope field on the slide as shown in FIGS. 10A–11B and accompanying text in the parent case, U.S. Ser. No. 07/984,191 incorporated by reference herein.

The preparatory solution described herein substantially eliminates, or at least substantially minimizes the formation of crystals within the fixed urine or urological sample during shipment or storage. This solution will also be useful as a cell preservative for all kinds of cytologies and for promoting adherence of cells to examination slides.

The primary crystals inhibited by the method described herein are common phosphate and oxalate crystals comprising calcium and magnesium cations. Formation of certain rare crystalline forms may not be inhibited.

The term "inhibition of crystal formation" as used herein is defined as meaning both the inhibition of the formation of crystals containing calcium or magnesium, or the solubilization of such crystals which are already present, in urine samples which would otherwise form crystals under a range of temperatures including room temperature and refrigeration temperatures (e.g., about 4° C.) and during a range of time periods including immediately after collection of the sample, after 24 hours and after 48 hours or later in cases where fixation was performed using a commonly used non-crystallization inhibiting composition such as buffered alcohol instead of the composition described herein. Inhibition of crystal formation allows the urine to be stored and shipped with its cells preserved. In a preferred embodiment, the composition is designed to be mixed in equal volume (1:1) with the urine.

In a preferred version, the composition when used as a fixative and crystallization inhibitor comprises three components with optional fourth and fifth components. A first component is a preservative which kills most bacteria and other microorganisms and inhibits endogenous enzymatic degradation. A preferred preservative is ethanol and comprises 50% of the volume of the fixative. Other preservatives which may be used are alcohols such as methanol and isopropanol, and formaldehyde and other appropriate preservatives. The preservative may comprise from about 20% to about 95% of the fixative, preferably about 35% to 65% of the fixative, and more preferably about 45% to about 55% of the fixative.

A second component is a buffer for adjusting the pH of the solution to help retain characteristic morphology of the cells. The buffer has a pK preferably in the range of about 6 to about 7 but alternatively in the range of about 5 to about 6 or about 7 to about 8. A preferred buffer is 2-N-morpholino-2-hydroxypropane-sulfonic acid (MOPSO), 0.05 M (of the total fixative), which is also effective within a range of from about 0.01 M to about 0.2 M.

Examples of other buffers having the preferred pK range and which are effective in a concentration range of about 0.01 M to 0.2 M of the fixative are N-[2-Acetamido]-2-aminoethanesulfonic acid) (ACES), (N-[2-Acetamido]-2-iminodiacetic acid) (ADA), (bis[2-Hydroxyethyl]imino-tris [hydroxymethyl]methane (BIS-TRIS), (2-[N-Morpholino] ethanesulfonic acid (MES), and (Piperazine-N,N'-bis[2-ethanesulfonic acid] (PIPES). Buffers in the alternate pK range of 7–8 are (N,N-bis [2-Hydroxyethyl]-2-aminoethanesulfonic acid) (BES), (3-[N,N-bis(2-Hydroxyethyl)amino]-2-hydroxypropanesulfonic acid) (DIPSO), (N-[2-Hydroxyethyl]piperazine-N'-[3-propanesulfonic acid] (EPPS), (N-[2-Hydroxyethyl] piperazine-N'-[2-ethanesulfonic acid] (HEPES), (N-[2-Hydroxyethyl]piperazine-N'-[2-hydroxypropane-sulfonic acid]) (HEPPSO), (3-[N-Morpholino]propanesulfonic acid) (MOPS), (Piperazine-N,N'-bis[2-hydroxypropanesulfonic acid]) (POPSO), (3-[N-tris(Hydroxymethyl)methylamino]-2-hydroxypropane-sulfonic acid) (TAPSO), and (N-tris [Hydroxymethyl]methyl-2-aminoethanesulfonic acid) (TES). These buffers are commercially available from a source such as Sigma Chemical Co.

A third component of the fixative, preferably comprising a concentration of from about 0.01 M to about 0.1 M in the fixative is a crystal-inhibiting agent for inhibiting formation, and for solubilization, of crystals. This invention contemplates any agent which chelates calcium or both calcium and magnesium and which is soluble in the fixative at the concentration of the preservative described herein. The invention also contemplates a combination of a calcium chelator with a magnesium chelator. Where the preservative is ethanol or another alcohol, the crystal-inhibiting agent should be soluble in the ethanol or the other alcohol where the preservative is provided in a concentration sufficient to be effective as a preservative. A preferred crystal-inhibiting agent is a tetraacetic acid derivative such as the dipotassium salt of ethylenediaminetetraacetic acid (EDTA) which in a preferred embodiment is soluble in 50% ethanol. Other EDTA salts comprising sodium, cesium, rubidium, and various organic cations may also be effective. Other effective crystal-inhibiting agents include, but are not limited to other derivatives of tetraacetic acid such as the potassium, cesium and rubidium salts of 1,2-bis(2-aminophenoxy) ethane-N,N,N', N'-tetraacetic acid (KBAPTA), ethylene glycol-bis [beta-aminoethyl ether]-N,N,N',N'-tetraacetic acid (KEGTA) and trans-1,2-diamino cyclohexane-N,N, N'N'-tetraacetic acid (KCDTA). Sodium salts of these compounds which are soluble in the preservative at the preservative concentration in the fixative are also effective.

An optional fourth component. is a substance to maintain the ionic strength within limits that inhibit cell distortion. A specific example is KCl (e.g., at a suggested concentration of about 0.10 M of the total fixative), and it must be both soluble in the preservative (e.g., ethanol) and not cause precipitation of the crystal-inhibiting agent (e.g., potassium EDTA or derivatives). Alternatively, the substance for maintaining the ionic strength may be an additional amount of the buffer previously added or another compatible buffer.

An optional fifth component is a biocide for preventing the growth of certain resistant bacteria and other microorganisms. A specific example is $NaN_3$, sodium azide, 0.1% (w/v) and ranging from about 0.02 to about 0.5%. This biocide component is optional depending on the time lapse between collection, shipment and analysis.

EXAMPLE 1

In one version, the fixative is prepared by mixing the aqueous components (at least the crystal-inhibiting agent and a buffer) and adjusting the pH of the solution (e.g., to about 6.5), then adding a quantity of ethanol, which in a preferred embodiment is equal in volume to the total volume of the other components. In an especially preferred embodiment the fixation composition comprises 0.01 M KEDTA, 0.05 M MOPSO, 0.1 M KCl, sodium azide (0.1%) and 50% ethanol (i.e., a volume of ethanol equal to the volume of the other combined components). The recipe for making this preferred embodiment is:

(1) Combine 298.2 g KCl, 450.8 g of MOPSO and 3630 ml DDW forming MOPSO buffer solution;

(2) Combine 3600 ml DDW, 14.74 g Dipotassium EDTA, 0.8 g Sodium Azide, and 400 ml of the MOPSO buffer solution. Adjust the pH to about 6.5 with KOH, to form Modified MOPSO buffer solution;

(3) Combine 1896 ml of the Modified MOPSO buffer solution with 2104 ml of Ethanol, to form the crystal-inhibiting fixative.

Additional fixation of cells to ensure preservation of protein markers can be achieved by first mixing the urological sample (e.g., urine) with a formaldehyde solution (for example, to a final formaldehyde concentration of about 0.5% to about 2% (w/v)) and allowing the urine/formaldehyde mixture to stand for an effective time period prior to addition of the above crystal-inhibiting fixative. The time period is preferably about 15 minutes but may range from about 5 minutes to about 30 minutes.

In an alternative version of the invention cells (not limited to cells from urological samples) may be fixated then treated to enhance their permeability by first being treated with a formaldehyde solution as described above, then treated with an alcohol solution comprising from 20% to 95% of the alcohol, as noted above. The cells are then ready to be treated to apply markers to the cell proteins.

The invention as presently described further contemplates improving the adherence of cells to glass examination slides by imparting or enhancing the negative charge on the surface of the cell membranes prior to deposition of the cells onto the examination slides.

Cytologists have long been plagued by an inability to maximize the number of cells on a slide prepared for examination of cellular characteristics, as noted above. Even in cases in which crystals are not a major contaminating factor, it may still prove difficult to optimize the number of cells which finally adhere to the examination slide.

Surprisingly, it has been discovered that the same component described elsewhere herein which acts as a crystal-inhibiting agent also is effective in improving the adherence of the cells to the slide by increasing the surface negative charge on the cell membranes. Thus the crystal-inhibiting agent is also a cell adherent agent for enhancing the slide-adherent capabilities of cytological samples.

EXAMPLE 2

The cell adherent/crystal-inhibiting agent can be used along with a preservative such as ethanol or any other preservative listed herein in a preliminary "cell wash" step (e.g., when resuspending cells after centrifugation) in the preparation of a cell sample for cytological examination. For example, the adherent agent may be used in a cell wash composition in the preparation of cells from a urine sample listed in the steps below:

(1) Concentrate the fixed urine sample by centrifugation. If sample is frozen at −70° C., thaw samples.

(2) Combining pellets into one 50 ml conical polypropylene centrifuge tube rinsing each tube after pellet transfer with 5–10 ml of Cell Wash Fluid. If frozen: Agitate cryovial to resuspend cells and pour sample into a labeled 50 ml centrifuge tube; rinse cryotube with DDW.

(3) Aspirate cells in centrifuge tube to disperse cell clumps and discard transfer pipet.

(4) Fill centrifuge tube up to 50 ml mark with Cell Wash Fluid.

(5) Let set for 20 minutes.

In a preferred version the cell wash composition is prepared by combining 2947 ml of deionized distilled water, 7.37 g of dipotassium EDTA, adjusting the pH to 5.5, e.g., with KOH, and adding the mixture to 1053 ml of 95% Ethanol.

EXAMPLE 3

The adherent agent may be used alone in a cell adherent composition in a final step in a cell preparation procedure for preparing the cells for application to a slide as shown in the steps below:

(1) Thoroughly mix a cell sample and count so that not more than 45,000 cells are placed in a filtration funnel. The number of cells on a slide required for proper coverage will vary with the cell type and must be determined empirically for samples other than urothelial cells.

(2) Place a Nuclepore filter into a filtration column and clamp into place. An 8 micron filter is used for urine samples, a 5 micron filter for cultured cells. Other applications will require empirical determination of the maximum size that will not pass the cells of interest. The column is obtained from Millipore and holds 15 ml of fluid.

(3) Pour the calculated amount of specimen into the filtration funnel and gently vacuum, being careful not to let the filter air dry, until about 2.0 mm of liquid remains.

(4) Rinse the funnel with approximately 15.0 ml of Cell Adherent Fluid (containing the adhering agent).

(5) Pour approximately 5.0 ml of modified Saccommano fixative into funnel and let sit for two minutes.

(6) Label two Probe-On slides: one "+" and one "−".

(7) Lift the filter off with clean forceps and place on Probe-on slide with cell side facing down. Uncharged slides are preferred because charged slides tend to bind antibody reagents, thereby leading to excess background fluorescence.

(8) Gently press down on the positive slide with a moistened Kimwipe for seven seconds.

(9) Place two drops of the Cell Adherent Fluid on the negative slide.

(10) Lift the filter off of positive slide; spray 2–3 times with Carbofix-E (Statlabs, Inc.).

(11) Place the filter on the negative slide and gently press with moistened Kimwipe for seven seconds.

(12) Lift the filter off slide and spray with Carbofix-E (Statlabs, Inc.).

(13) Let slides dry for at least fifteen minutes prior to freezing.

(14) Slides may be stored frozen at −20° C. for a maximum of two weeks.

In a preferred version of the cell adherent composition, 7.36 g of dipotassium EDTA is added to 4000 ml of deionized distilled water, and 0.8 g of sodium azide (optionally) as a biocide. The pH is adjusted to 5.5 and the composition is stored at −20° C., then thawed before use.

Any of these procedures (crystal-inhibition, cell washing, final cell adherent preparation) can be used in isolation or in combination to improve the number of cells which adhere to the slide. These procedures, taken individually or in combination often result in as much as a 70% or more increase in the number of cells which ultimately adhere to the examination slide. In a preferred version, in any one of the compositions, including the crystal-inhibiting fixative, the cell wash composition, and the cell adherent fluid, the active ingredient, e.g., KEDTA, preferably comprises (but is not limited to) a concentration of from about 0.01M to 0.1M of the total solution.

EXAMPLE 4

The efficacy of the crystallization inhibiting formulation of the present invention is shown in the photomicrographs of FIGS. 1–6. Various versions of the present invention were compared to a non-crystal-inhibiting fixative (FIG. 1) and to a fixative with a commercial chelating resin (FIG. 2).

To prepare these microphotographs, a urine sample was collected and seeded with sufficient oxalate to ensure formation of crystals. Separate portions of the urine sample were then fixated with 0.05 M MOPSO and 0.10 M KCl. Samples represented by FIGS. 3–6 were treated with a fixative having a crystal-inhibiting agent at 0.01 M.

FIG. 1 shows that in the absence of any soluble crystal-inhibiting agent, large numbers of crystals formed. A small reduction was achieved by adding a chelating resin (FIG. 2). Virtually all of the small crystals were inhibited by fixatives containing KEDTA, KEGTA, KCDTA (FIGS. 3–5). The fixative with KBAPTA appeared to completely prevent the formation of crystals (FIG. 6).

EXAMPLE 5

Another study was conducted in which 50 slides were prepared from urine samples fixated with a preferred crystal-inhibiting fixative of the present invention, and another 50 slides were prepared from urine samples fixated with a control fixative lacking a crystal-inhibiting agent (e.g., the fixative was ethanol buffered with MOPSO, see, for example the reference by McGowan, et al., "Equilibrium Binding of Hoechst 33258 and Hoechst 33342 Fluorochromes with Rat Colorectal Cells", *The Journal of Histochemistry and Cytochemistry*, Vol. 36, No. 7, 1988, pp. 757–762). The urine samples were taken from the same population. On the slides made using samples preserved with the crystallization inhibiting fixative, there was an average of 165 cells adhered per $mm^2$. On the slides made using samples preserved by the control fixative without a crystal-inhibiting agent, there was an average of only 33 cells adhered per $mm^2$. Thus, inhibition of crystallization in the urine improved adherence of cells to the slide by a factor of 5x.

EXAMPLE 6

Another version of the invention contemplated herein is an easy to use kit. The kit contains a container for receiving a quantity of urine or other fluid containing cells. The container may be a jar or cup equipped with a fastener cover or the container may be a bag, or any other container adapted for receiving and containing a urine sample. The kit further contains a quantity of a crystal-inhibiting fixative such as any of those described elsewhere herein for adding to the urine after the urine has been disposed into the container. The kit may optionally include a quantity of another fixative such as formaldehyde for addition to the urine prior to addition of the crystal-inhibiting fixative.

In a preferred version, the kit includes a graduated 250 ml container, a vial containing about 0.5 ml of formaldehyde, and a container with about 100 ml of crystal-inhibiting fixative, such as any of the fixative versions described elsewhere herein. The kit is used by placing about 100 ml of urine into the urine collection container then adding the formaldehyde or other fixative (if formaldehyde or another fixative comprises part of the kit). This mixture is swirled then left to stand for about 15 minutes. Then, a volume of the crystal-inhibiting fixative about equal to the volume of the urine mixture is added and mixed. The container is then closed in preparation for shipment or further analysis.

The kit described herein may also be used for treating a bladder wash sample in the same manner it is used to treat a urine sample.

Changes may be made in the construction and the operation of the various compositions and kits described herein or in the steps or the sequence of steps of the methods described herein without departing from the spirit and scope of the invention as defined in the following claims.

What is claimed is:

1. A method of treating cells, comprising:

providing a suspension of cells;

exposing the cells to a treatment solution comprising a tetraacetic acid derivative, the derivative having a negative charge when in ionic form wherein a negative surface charge is imparted to the cells; and disposing the cells upon a surface of an examination slide wherein the cells have enhanced adherence to the surface of the examination slide due to exposure to the treatment solution.

2. The method of claim 1 wherein the treatment solution further comprises a preservative.

3. The method of claim 1 wherein the treatment solution further comprises a biocide.

4. The method of claim 1 wherein the tetraacetic acid derivative is at least one of KEDTA, KBAPTA, KEGTA, KCDTA and NaEDTA.

5. The method of claim 1 wherein the treatment solution has a pH in the range of from about 5 to about 7.

6. A method of treating cells, comprising:

providing a urine sample containing cells;

exposing the urine sample to a treatment solution comprising a tetraacetic acid derivative, the derivative having a negative charge when in ionic form wherein a negative surface charge is imparted to the cells; and disposing the cells upon a surface of an examination slide wherein the cells have enhanced adherence to the surface of the examination slide due to exposure to the treatment solution.

7. The method of claim 6 wherein the treatment solution further comprises a preservative.

8. The method of claim 6 wherein the treatment solution further comprises a biocide.

9. The method of claim 6 wherein the tetraacetic acid derivative is at least one of KEDTA, KBAPTA, KEGTA, KCDTA and NaEDTA.

10. The method of claim 6 wherein the treatment solution has a pH in the range of from about 5 to about 7.

11. A method of treating bladder, prostate or kidney cells, comprising:

providing a suspension of bladder, prostate or kidney cells;

exposing the bladder, prostate or kidney cells to a treatment solution comprising a tetraacetic acid derivative, the derivative having a negative charge when in ionic form wherein a negative surface charge is imparted to the bladder, prostate or kidney cells; and disposing the bladder, prostate or kidney cells upon a surface of an examination slide wherein the bladder, prostate or kidney cells have an enhanced adherence to the surface of the examination slide due to exposure to the treatment solution.

12. The method of claim 11 wherein the treatment solution further comprises a preservative.

13. The method of claim 11 wherein the treatment solution further comprises a biocide.

14. The method of claim 11 wherein the tetraacetic acid derivative is at least one of KEDTA, KBAPTA, KEGTA, KCDTA and NaEDTA.

15. The method of claim 11 wherein the treatment solution has a pH in the range of from about 5 to about 7.

* * * * *

UNITED STATES PATENT AND TRADEMARK OFFICE
CERTIFICATE OF CORRECTION

PATENT NO. : 6,372,450 B1 Page 1 of 1
APPLICATION NO. : 09/711495
DATED : April 16, 2002
INVENTOR(S) : George P. Hemstreet, III, Robert E. Hurst and Rebecca B. Bonner It is certified that error appears in the above-identified patent and that said Letters Patent is hereby corrected as shown below:

On the Title Page item (62), Under the Heading "Related U.S. Application Data" : After the words, "which is a " delete "division" and insert -- continuation --.

Signed and Sealed this

Twenty-eighth Day of August, 2007

JON W. DUDAS
*Director of the United States Patent and Trademark Office*